US00PP09463P

United States Patent [19]

Challet

[11] Patent Number: Plant 9,463

[45] Date of Patent: Mar. 5, 1996

[54] CHRYSANTHEMUM PLANT NAMED 'CHALECAT'

[75] Inventor: Jean-Pierre Challet, Lafayette, Calif.

[73] Assignee: Selection New Plant Sarl, Le Cannet Des Maures, France

[21] Appl. No.: 273,998

[22] Filed: Jul. 12, 1994

[51] Int. Cl.[6] ..... A01H 5/00

[52] U.S. Cl. ..... Plt./76

[58] Field of Search ..... Plt./74.1, 76, 81, Plt./82, 80

[56] References Cited

U.S. PATENT DOCUMENTS

| | | | |
|---|---|---|---|
| P.P. 2,119 | 1/1962 | Lamborot | Plt./76 |
| P.P. 3,218 | 6/1972 | Vogel | Plt./82 |
| P.P. 3,890 | 5/1976 | Jessel, Jr. et al. | Plt./76 |
| P.P. 8,898 | 9/1994 | Gilcenštein | Plt./76 |

*Primary Examiner*—Howard J. Locker

*Attorney, Agent, or Firm*—Burns, Doane, Swecker & Mathis

[57] ABSTRACT

A new and distinct Chrysanthemum cultivar named 'Chalecat' is provided. The new cultivar was the result of a controlled breeding program. Attractive very large double incurved blossoms of the pompon type are formed that are cherry pink on the inner surface and light pastel pink on the outer surface. The incurving is particularly pronounced at the tips of the ray florets. The blossoms are long lasting and keep their form for approximately three weeks. The response period of the flowers is approximately nine weeks. Recurrent profuse flower production throughout the year is possible. The plant possesses strong stems, forms large dark green leaves, and commonly assumes a height of approximately 45 to 50 cm. The blossom coloration contrasts nicely with the dark green foliage. The new cultiver is particularly suited for use in the production of a decorative pot Chrysanthemum that grows well single stem or disbudded. No growth regulator is necessary to achieve the short to medium plant height.

4 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chalecat'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during October 1975 at Nusille, Trementines, France. The female parent (i.e., the seed parent) was the 'Siky' cultivar (non-patented in the United States) having a large pink incurved flower, a response period of nine weeks, and a tall plant height that was bred by Durand of France many years ago, and the male parent (i.e., the pollen parent) was the 'Prouesse' cultivar (non-patented in the United States) which is a very old French cultivar bred by an unknown breeder having large incurved and reflexed flowers that are red on the inside and bronze on the outside, and a response period of 10 weeks. The parentage of the new cultivar can be summarized as follows:

'Siky'×'Prouesse'.

The seeds resulting from the above pollination were sown and many small plantlets were obtained which were physically and biologically different from each other. Selective study resulted in the identification of a single plant of the new variety.

It was found that the new cultivar of the present inventions:

(a) exhibit attractive large double incurved pompon blossoms that are cherry pink on the inner surface and light pastel pink on the outer surface, (b) exhibits a flower response period of approximately nine weeks, (c) forms attractive dark green glossy foliage, (d) achieves a short to medium plant height, and (e) is particularly suited for pot mum production on a recurrent basis throughout the year.

The new cultivar is inteded primarily as a decorative pot Chrysanthemum for growing indoors. However, it also can be grown for cut flower production in those instances where stems of approximately 40 cm. are acceptable. Also, the new cultivar can be grown outdoors at temperatures above freezing.

In the absence of debudding commonly 6 to 10 blossoms form per stem. The new cultivar can be grown single-stem or disbudded. An increased number of branches readily can be induced by pinching. The pinching of a cutting commonly produces 3 to 4 stems per cutting. No growth regulator is required to produce the short to medium plant height; however, a growth regulator optionally can be utilized.

The new cultivar can be considered to be an October-flowering greenhouse variety with the natural flowering season commonly occurring in weeks 42 and 43 of the year. Attractive blossoms can be produced on a recurrent basis throughout the year with the indicated nine week response period. The blossoms are long lasting and commonly can be maintained on the plant for approximately three weeks.

Asexual reproduction of the new cultivar by cuttings initially taken during 1976, as performed in Nuaille, Trementines, France, in a controlled environment has demonstrated that the characteristics of the new cultivar as herein described are firmly fixed and are retained through successive generations of asexual propagation.

'Chalecat' has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the 'Peacock' cultivar (non-patented in the United States), the 'Chalecat' cultivar is found to exhibit a faster response period of approximately 9 week vs. 10 weeks, a shorter plant height, and a better propensity for branching.

Mutations of the 'Chalecat' cultivar are the 'Chahalu' cultivar (copening U.S. Plant patent application Ser. No. 08/273,996 filed Jul. 12, 1994), the 'Chatupa' cultivar (copneding U.S. patent application Ser. No. 08/273,997, filed Jul. 12, 1994), and the 'Chalurido' cultivar (copending U.S. patent application Ser. No. 273,999 filed Jul. 12, 1994). Each of these additional cultivars can be readily distinguished from the patent 'Chalecat' cultivar with respect to a number of plant characteristics.

For instance, the 'Chahalu' cultivar exhibits a lemon yellow capitulum unlike the 'Chalecat' cultivar, a foliage coloration between Green Group 137A and 139A unlike the Yellow-Green Group 147A coloration of the 'Chalecat' cultivar, a stem coloration of the Yellow-Green Group 144A unlike the Yellow-Green Group 146B of the 'Chalecat' cultivar, an angular stem cross-section unlike the round cross-section of the 'Chalecat' cultivar, course serration unlike the medium to fine serration of the 'Chalecat' cultivar, and a diverging margin of sinus between lateral leaf lobes generally unlike the 'Chalecat' cultivar.

The 'Chatupa' cultivar exhibits a honey gold capitulum unlike the 'Chalecat' cultivar, commonly forms a generally larger capitulum than the 'Chalecat' cultivar, a foliage coloration of Green Group 137A unlike the Yellow-Green Group 147A coloration of the 'Chalecat' cultivar, a stem coloration between Yellow-Green Group 144A and 144B unlike the Yellow-Green Group 146B coloration of the 'Chalecat' cultivar, medium leaf serration unlike the medium to fine serration of the 'Chalecat' cultivar, and a leaf base shape of rounded tending to cordate unlike the 'Chalecat' cultivar.

The 'Chalurido' cultivar exhibits a capitulum having inner surfaces of Venetian violet and silvery lavender outer surfaces unlike the 'Chalecat' cultivar that has cherry pink inner surfaces and light pastel pink outer surfaces, commonly forms a fully opened capitulum having a generally smaller diameter than the 'Chalecat' cultivar, a stem coloratin of Yellow-Green Group 144A unlike the Yellow-Green Group 146B coloration of the 'Chalecat' cultivar, a more variable fine to coarse leaf serration than the 'Chalecat' cultivar, an angular stem cross section unlike the round stem cross sections of the 'Chalecat' cultivar, approximately 37 to 40 leaves per typical stem in a long day crop before the bud opens unlike the lesser number of approximately 29 to 32 for the 'Chalecat' cultivar, a greater variation in the converging margin of sinus between lateral lobes than the 'Chalecat' cultivar, and a generally asymmetric leaf base unlike the 'Chalecat' cultivar.

The new 'Chalecat' cultivar is being marketed under the Rose Cymbal trademark.

BRIEF DESCRIPTION OF THE PHOTOGRAPHS

The accompanying photographs were prepared during June, 1994, and show as nearly true as it is reasonably possible to make the same in color illustrations of this character, typical plants and plant parts of the new cultivar of the present invention. The plants were 12 weeks of age and were grown at Nuaille, Trementines, France, under standard greenhouse conditions which approximate those commonly utilized for the production of decorative pot mums. The plant had been disbudded in order to encourage the formation of one large bloom per stem. There had been one application of Alar growth regulant at a concentration of 3 grams per liter. Any labels shown in the photographs are 2.5 cm. in width and can be used for size comparisons.

DETAILED DESCRIPTION

Figure 1:
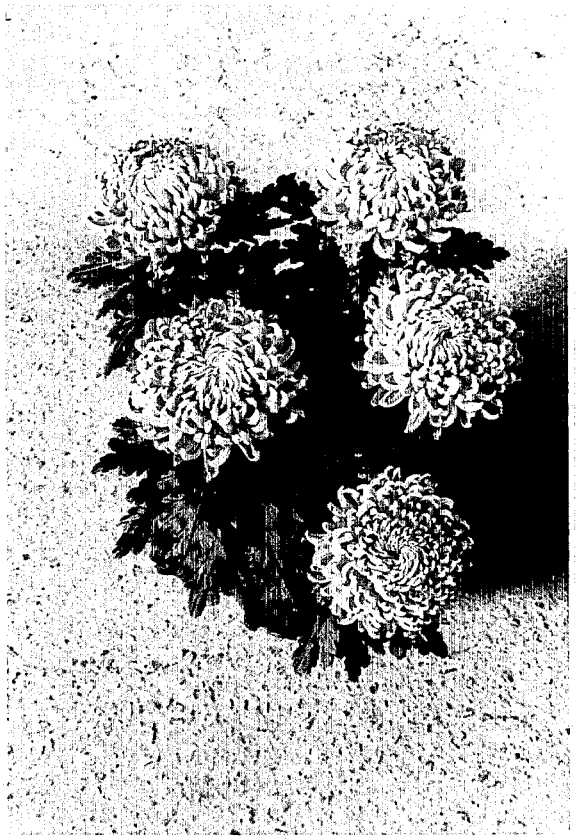
FIG. 1 illustrates typical specimens of the overall plant wherein four cuttings were placed in a 20 cm. pot. The large incurved flowers having cherry pink petals and pastel pink reverse tones generally in the form of large round balls, as well as the foliage, are apparent.
Figure 2:
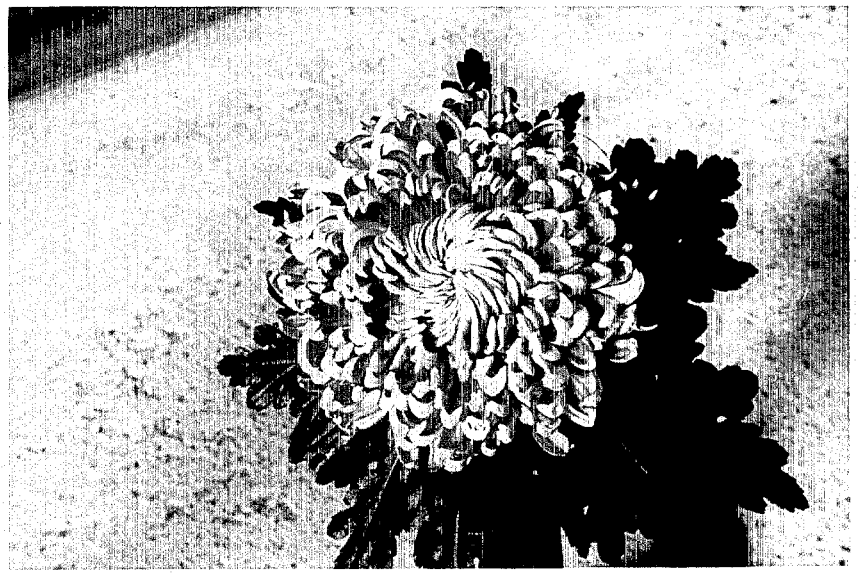
FIG. 2 illustrates a closer view of a typical flower in the course of opening.
Figure 3:
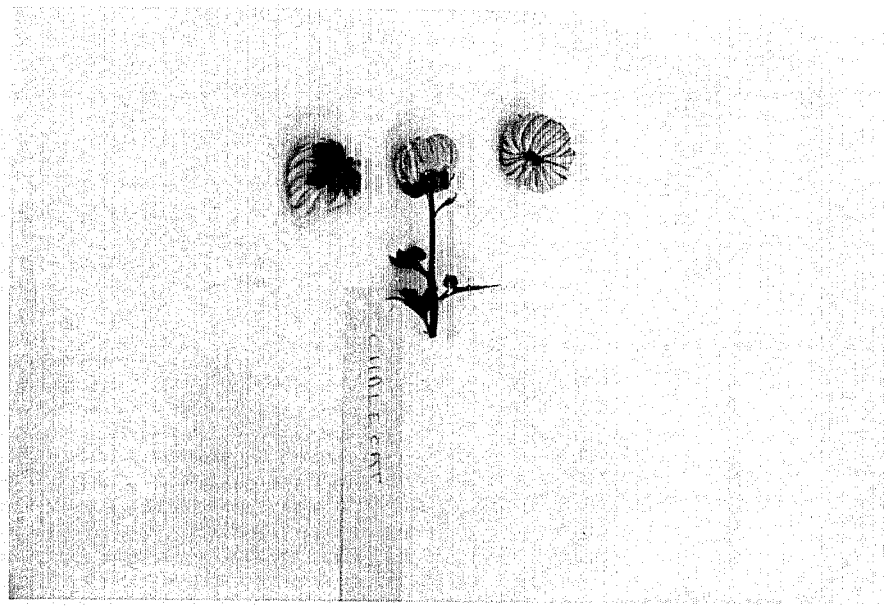
FIG. 3 illustrates from left to right, under, side, and top views of unopened buds.
Figure 4:
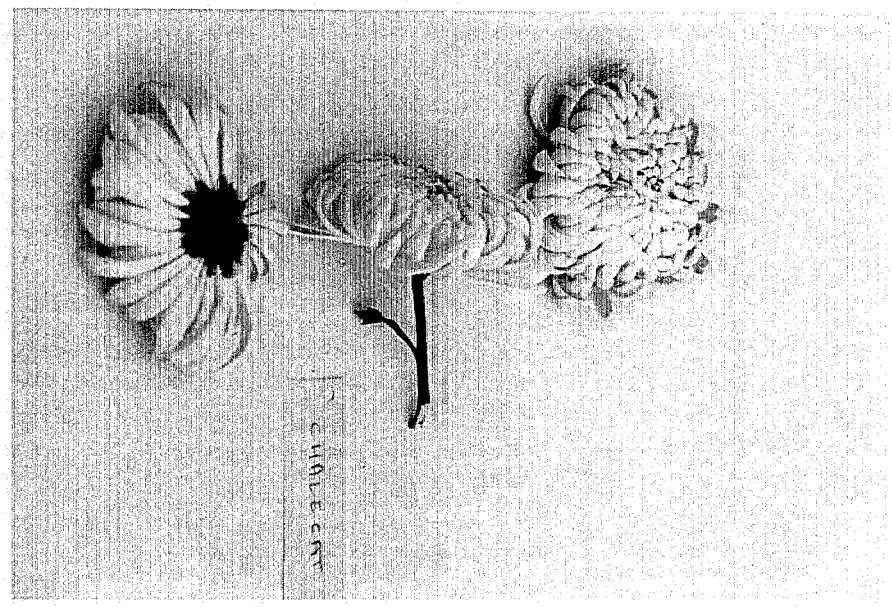
FIG. 4 illustrates from left to right, under, side, and top views of the flowers as opening begins.
Figure 5:
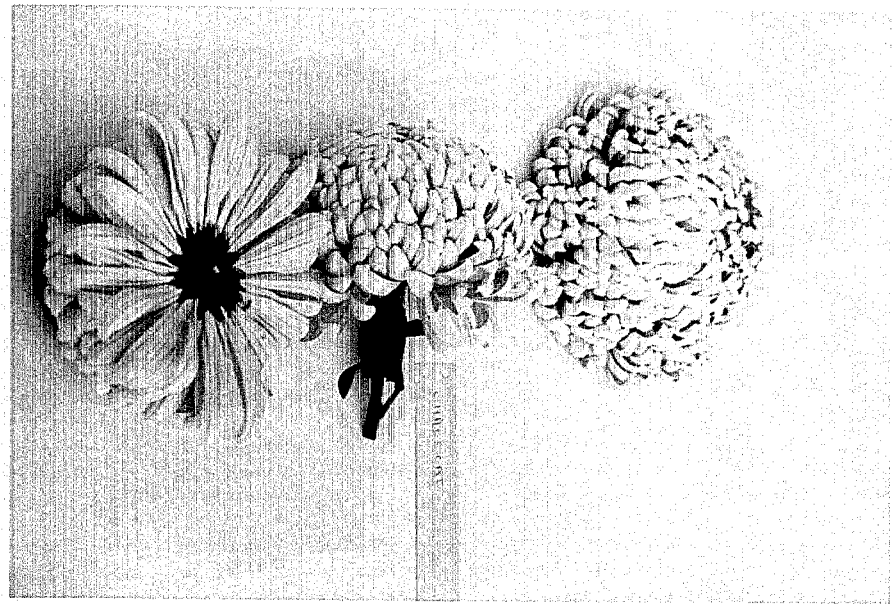
FIG. 5 illustrates from left to right, under, side, and top views of flowers in a more advanced stage of opening.
Figure 6:
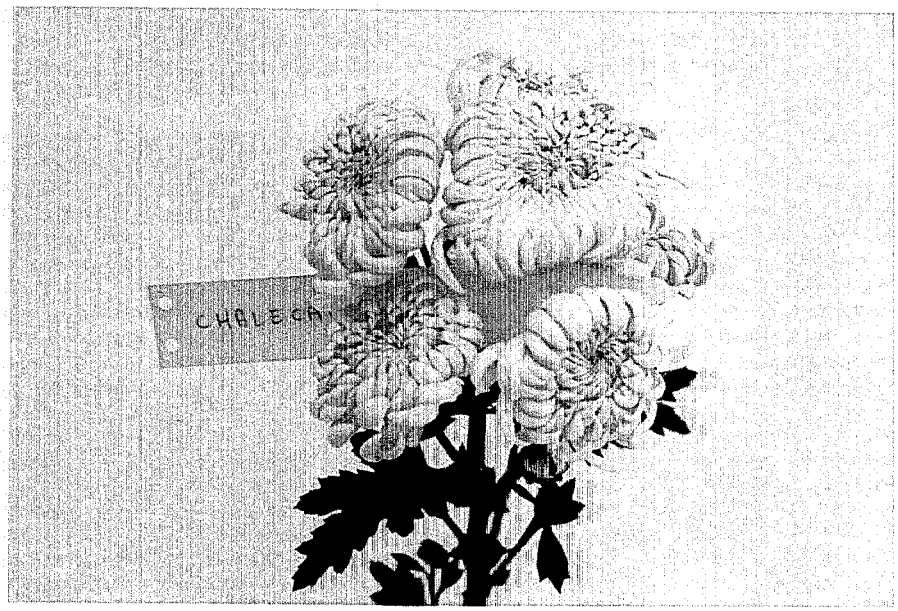
FIG. 6 illustrates a typical spray of flowers as opening begins.
Figure 7:
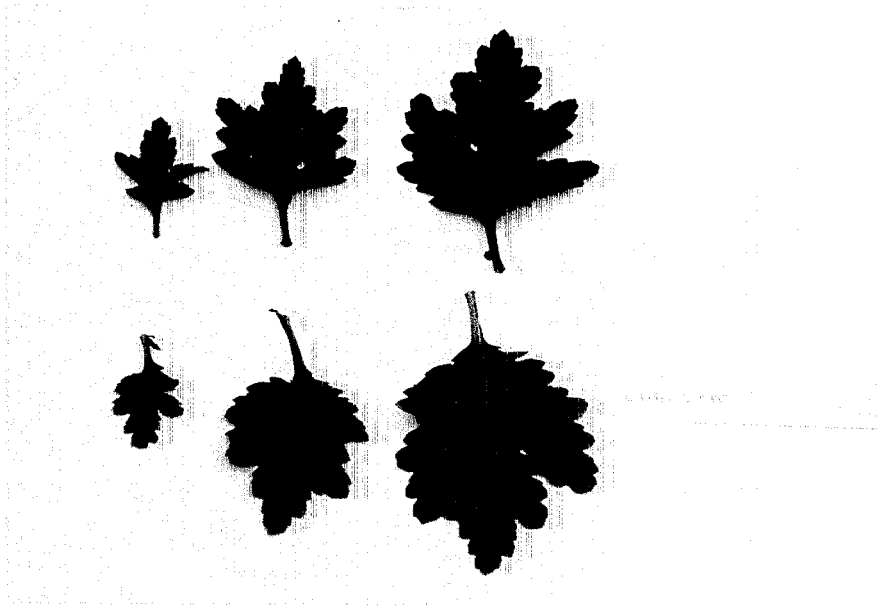
FIG. 7 illustrates as the top row, the upper surfaces of typical leaves of various sizes, and at the bottom row the under surfaces of typical leaves of various sizes.

The chart used in the identification of colors described hereafter is The R.H.S. Colour Chart of The Royal Horticultural Society, London, England. In some instances more common color terms are provided and are to be accorded their usual dictionary significance. The plants described were 12 weeks of age and were grown at Nuaille, Trementines, France, under standard greenhouse conditions which approximate those commonly utilized for the production of decorative pot mums.

Classification:

*Botanical—Dendranthema grandiflora*, cv. 'Chalecat'.

*Comercial.*—Decorative pot mum.

INFLORESCENCE

A. Capitulum:

*Form.*—Large, double, incurved, and commonly exhibiting a perfect configuration. The incurving is particularly strong at the tips.

*Type.*—Pompon.

*Diameter across face.*—Approximately 14 to 15 cm. on average when fully expanded.

B. Corolla of ray and disc florets:

*Color of bud.*—Commonly near Purple Group 75A and 75B on the outside when opening.

*Disc florets.*—Tubular, few in number, very difficult to observe, and tend to be scattered among the ray florets with a small cluster at the apex of the receptacle that is visible only when the ray florets are removed.

*General tonality.*—Light pastel pink when the outside of the florets is observed, and darker cherry pink when the inside of the florets is observed.

*Color ray florets.*—When the blossoms are mature, the outer rows of florets commonly exhibit an inner surface of Red-Purple Group 75D overlaid with Red-Purple Group 72B, and an outer surface of Purple Group 75D with tints of Red-Purple Group 72B. When the blossoms are mature, the inner rows of florets commonly exhibit an inner surface of Red-Purple Group 73D overlaid with Red-Purple Group 71B and fading to lighter than Purple Group 75D, and an outer surface of Red-Purple Group 65D lightly overlaid with Red-Purple Group 64B.

*Configuration ray florets.*—Concave in cross section, textured, posses pointed and sometimes dentated tips, and approximately 59 mm. in length and approximately 10 mm. in width on average.

C. Reproductive organs:

*Androecium.*—Generally present with disc florets and absent in ray florets.

*Gynoecium.*—Generally present with most disc florets and with most ray florets.

*Pollen.*—Formed in a slight quantity and golden-yellow in coloration.

*Fragrance.*—Typical of Chrysanthemum.

PLANT

A. General appearance:

*Height.*—Short to medium and approximately 45 to 50 cm. in height on average.

B. Foliage:

*Color(upper surface).*—Dark green, Yellow-Green Group 147A, and glossy.

*Color(under surface).*—Lighter green, approaches Green Group 138A.

*Long day leaf count.*—Approximately 29 to 32 leaves per typical stem in a long day crop before the bud occurs.

*Configuration.*—Lobed (as illustrated).

*Texture.*—Fleshy.

*Serration*—Medium to fine.

*Internode length.*—Approximately 16 mm. on average.

*Stems.*—Strong, round in cross section and generally solid, medium pubescence, nearest to Yellow-Green Group 146B in coloration, and commonly with anthocyanin coloration mainly at the base, near Greyed-Purple Group 187A.

*Apex.*—Acuminate.

*Base.*—Acute or slightly rounded.

*Claw in base of sinus between lateral lobes.*—Absent.

*Margins of sinus between lateral lobes.*—Converging, but occasionally diverge.

I claim:

1. A new and distinct cultivar of Chrysanthemum plant named 'Chalecat', substantially as herein shown and described, which (a) exhibits attractive large double incurved pompon blossoms that are cherry pink on the inner surface and light pastel pink on the outer surface, (b) exhibits a flower response period of approximately nine weeks, (c) forms attractive dark green glossy foliage, (d) achieves a short to medium plant height, and (e) is particularly suited for pot mum production on a recurrent basis throughout the year.

* * * * *